United States Patent
Meyer

(10) Patent No.: US 10,799,203 B2
(45) Date of Patent: Oct. 13, 2020

(54) METHOD FOR ACQUIRING X-RAY DATA, X-RAY DEVICE, COMPUTER PROGRAM AND ELECTRONICALLY READABLE STORAGE MEDIUM

(71) Applicant: Siemens Healthcare GmbH, Erlangen (DE)

(72) Inventor: Andreas Meyer, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 107 days.

(21) Appl. No.: 16/018,584

(22) Filed: Jun. 26, 2018

(65) Prior Publication Data
US 2018/0368798 A1    Dec. 27, 2018

(30) Foreign Application Priority Data
Jun. 27, 2017  (EP) ..................... 17178141

(51) Int. Cl.
*A61B 6/00*  (2006.01)
*A61B 5/0402*  (2006.01)
(Continued)

(52) U.S. Cl.
CPC .......... *A61B 6/5205* (2013.01); *A61B 5/0402* (2013.01); *A61B 5/0456* (2013.01);
(Continued)

(58) Field of Classification Search
CPC ..... A61B 6/504; A61B 6/5235; A61B 6/5264; A61B 5/7285; A61B 6/032; A61B 6/12;
(Continued)

(56) References Cited

U.S. PATENT DOCUMENTS 6,459,755 B1 * 10/2002 Li .......................... A61B 6/032
378/4
2007/0248262 A1   10/2007 Boese
(Continued)

FOREIGN PATENT DOCUMENTS

EP     3420911 A1    1/2019
WO    2008120119 A1  10/2018

OTHER PUBLICATIONS

C. J. Ritchie, Correction of computed tomography motion artifacts using pixel-specific back-projection, Jun. 1996, IEEE Transactions on Medical Imaging, vol. 15, No. 3. (Year: 1996).*
(Continued)

*Primary Examiner* — Brenda C Bernardi
(74) *Attorney, Agent, or Firm* — Lempia Summerfield Katz LLC

(57) ABSTRACT

A method and device for acquiring at least a part of an x-ray data set with at least one x-ray device. The x-ray data set includes at least one first x-ray image data set and at least one second x-ray image data set acquired separated in time that are to be evaluated together. Both x-ray image data sets show a region of interest of a patient that is subject to heart motion at different phases of a heart cycle. The second x-ray image data set is acquired triggered at a beginning of each heart cycle covered by the acquisition and with an acquisition rate such that the phases of the acquired x-ray image data set match phases of the first x-ray image data set.

17 Claims, 2 Drawing Sheets

(51) Int. Cl.
*A61B 6/12* (2006.01)
*A61B 5/00* (2006.01)
*A61B 5/0456* (2006.01)
*A61B 6/03* (2006.01)
*G06T 7/00* (2017.01)
*A61B 90/00* (2016.01)

(52) U.S. Cl.
CPC ............ *A61B 5/7285* (2013.01); *A61B 6/032* (2013.01); *A61B 6/12* (2013.01); *A61B 6/405* (2013.01); *A61B 6/463* (2013.01); *A61B 6/466* (2013.01); *A61B 6/481* (2013.01); *A61B 6/486* (2013.01); *A61B 6/487* (2013.01); *A61B 6/503* (2013.01); *A61B 6/504* (2013.01); *A61B 6/5235* (2013.01); *A61B 6/5264* (2013.01); *A61B 6/5288* (2013.01); *A61B 6/541* (2013.01); *A61B 6/545* (2013.01); *G06T 7/0016* (2013.01); *A61B 2090/376* (2016.02); *A61B 2576/023* (2013.01)

(58) Field of Classification Search
CPC ......... A61B 6/405; A61B 6/463; A61B 6/466; A61B 6/481; A61B 6/486; A61B 6/487; A61B 6/503; A61B 6/5288; A61B 6/541; A61B 6/545; A61B 6/0402; A61B 6/0456; A61B 6/5205; A61B 2090/376; A61B 2576/023; G06T 7/0016
See application file for complete search history.

(56) References Cited

U.S. PATENT DOCUMENTS

| | | | |
|---|---|---|---|
| 2008/0187092 A1* | 8/2008 | Boese | A61B 6/541 |
| | | | 378/8 |
| 2010/0027736 A1 | 2/2010 | Bruder et al. | |
| 2010/0074504 A1* | 3/2010 | Bruijns | A61B 6/481 |
| | | | 382/132 |
| 2014/0328462 A1 | 11/2014 | Uehara et al. | |
| 2015/0087972 A1 | 3/2015 | Dumont et al. | |
| 2015/0139388 A1 | 5/2015 | Liu | |
| 2019/0192104 A1* | 6/2019 | Thran | A61B 6/032 |

OTHER PUBLICATIONS

Dumont, Guillaume, and Peng Wang. "Dynamic overlay of anatomy from angiography to fluoroscopy." U.S. Appl. No. 14/444,120, filed Mar. 26, 2015.

European Search Report for European Patent Application No. 17178141.2-1124 dated Jan. 10, 2018.

European Form 2906 for European Application No. 18174980.5-1122/3420911 dated Jul. 3, 2020.

* cited by examiner

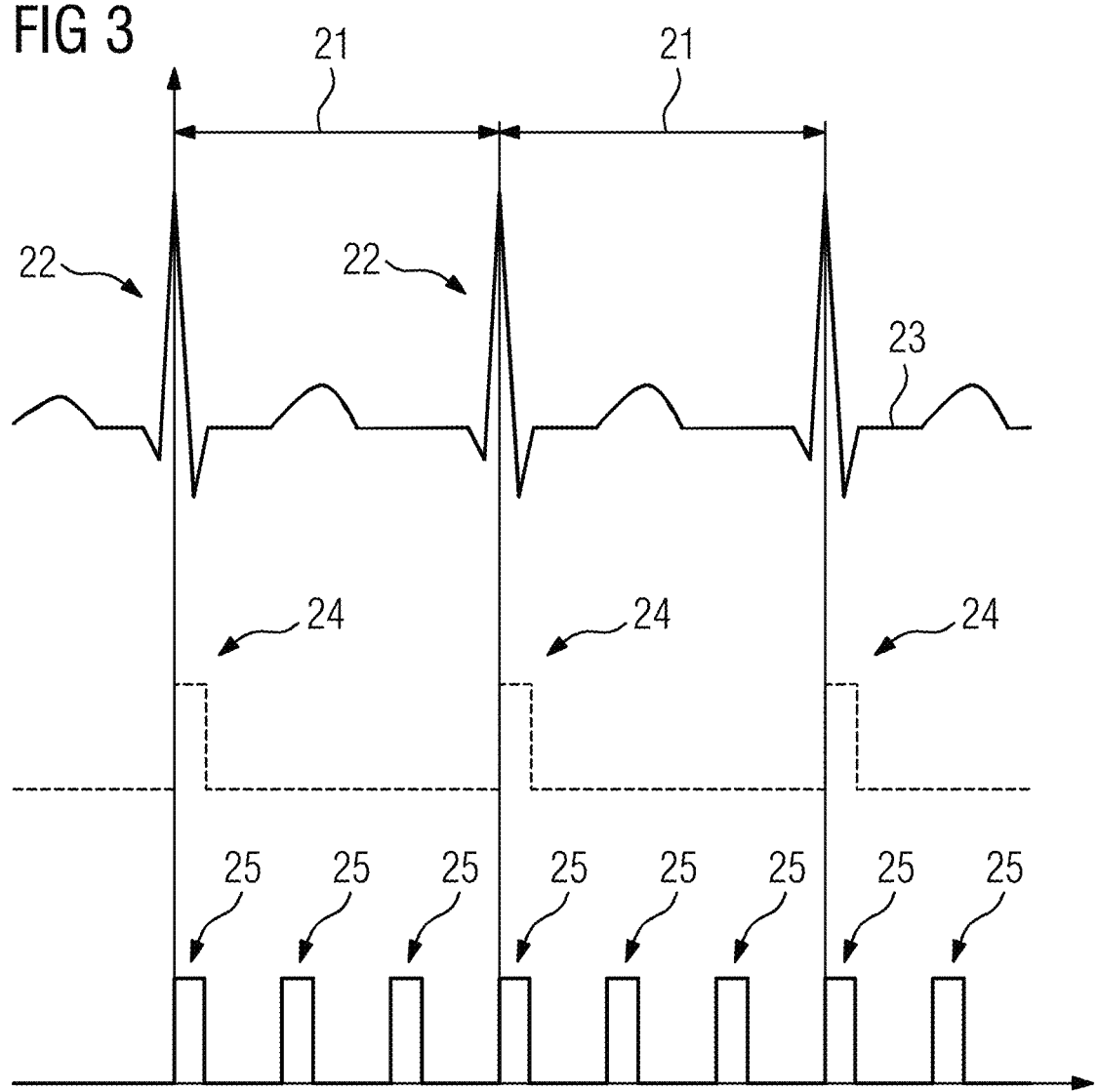

METHOD FOR ACQUIRING X-RAY DATA, X-RAY DEVICE, COMPUTER PROGRAM AND ELECTRONICALLY READABLE STORAGE MEDIUM

CROSS REFERENCE TO RELATED APPLICATIONS

This application claims the benefit of EP17178141.2 filed on Jun. 27, 2017, which is hereby incorporated by reference in its entirety.

FIELD

Embodiments relate to a method for acquiring at least a part of an x-ray data set with at least one x-ray device, the x-ray data set including at least one first x-ray image data set and at least one second x-ray image data set acquired separated in time, that are to be evaluated together, wherein both x-ray image data sets show a region of interest of a patient that is subject to heart motion, at different phases of a heart cycle.

BACKGROUND

Heart diseases close to the human heart, for example coronary artery chronic total occlusion (CTO), are one of the leading causes of death of patients. Thus, minimally invasive operation techniques have been developed to treat patients suffering from heart diseases. For example, to treat CTO, an available procedure is percutaneous coronary intervention (PCI), that relies on the insertion of a catheter through the obstructed artery to release the occlusion.

In general, instruments, for example catheters or guide wires, are introduced into the patient and guided to the heart structures, for example coronary blood vessels. During the intervention, the practitioner tracks the progress of the instruments in the blood vessels. As the instruments are well visible in x-ray images, for example in fluoroscopy images, navigation in the blood vessel system may be performed using fluoroscopy imaging. However, the anatomical structures of interest are more or less transparent to x-rays, meaning the structures are not visible in fluoroscopy images without using contrast agents. Contrast agents, however, empty from the region of interest very quickly due to blood flow, such that the following clinical workflow is used:

Acquire a contrast-enhanced first series of x-ray images,

Display a contrast-enhanced reference image from this series in parallel to a current fluoroscopy image using the same acquisition geometry, e.g. the same projection direction, Side-by-side guidance of the interventional instrument, tracking motion of the instrument in comparison to the displayed static contrast-enhanced reference image, Recurring, short contrast agent injections to provide for the correct path for the instrument in the vessel tree or the coronary chamber.

Other approaches segment interesting anatomical structures, for example heart structures, from previous contrast-enhanced acquisitions and view the segmentation results with current x-ray images, for example fluoroscopy images. In another technique, pre-operational image data, for example magnetic resonance data (MR data) or computer tomography data (CT data) are used for segmentation and overlay. The methods aim at reducing the amount of contrast agent during the procedure and providing a faster, safer and more precise intervention.

Fusion techniques and overlay techniques are used in the case of anatomical structures showing only little movement, for example in interventional neurological radiology. In this field, two dimensional or three-dimensional road map techniques are used to provide anatomical information and position information of the instrument in one fused or overlaid image during the interventional procedure.

However, known static fusion and overlay techniques do not allow precise fusion and/or overlay of interesting structures regarding the heart region of the patient, since the region is subject to heart motion and breathing motion. Thus, the motions have to be compensated when fusing and/or overlaying x-ray images of the anatomy and the instrument, or, in general, evaluating image data sets acquired separated in time together. In the case of interventional guidance during an operation, for example, a minimally invasive intervention, the movement compensating techniques are called dynamic road mapping techniques.

In US 2015/0087972 A1, dynamic overlay of anatomy modelled from multi-cycle (21) angiography to fluoroscopy, e.g. an overlay that changes over time with the heart and/or breathing cycles (21) of anatomical structures on fluoroscopy X-ray images, is provided. The dynamic overlay of the anatomy is based on fusing candidate overlays from a multi-cycle (21) angiography sequence and prediction. Candidate overlays of these anatomical structures on the fluoroscopy images are created based on angiographic anatomy from different cycles (21). By tracking the medical devices and anatomical structures during only a few heart cycles (21) in an angiography sequence, a model for their motion during the intervention is created. The position of anatomy across several frames in fluoroscopy imaging is predicted using the model for motion. By using the prediction model and the candidate overlays, the dynamic overlay of the anatomical structures on the fluoroscopy images is provided to assist the practitioners during surgical interventions.

The methods have certain disadvantages. For example, when overlaying x-ray images, inaccuracies occur, since, among others, the motion of the blood vessel is too fast, so that usual acquisition rates of for example 15 images per second do not suffice to sample the heart motion adequately. A possible solution is to increase the acquisition rate to obtain a sufficient sample frequency for the heart motion. This approach, however, is diametrically opposed to the trend of decreasing patient x-ray dose or to keep patient dose low, respectively.

SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a method for more robustly and accurately evaluating x-ray images associated with heart cycle phases together.

In an embodiment, at least the second x-ray image data set triggered at a beginning of each heart cycle covered by the acquisition and with an acquisition rate is acquired such that the phases of the acquired x-ray image data set match phases of the first x-ray image data set.

The first image data set includes images at equidistant phases of the heart cycle including one imaged phase that coincides with a beginning of the heart cycle that may be acquired triggered or by using corresponding reconstruction parameters during a reconstruction process. Including a first image data set, the second x-ray image data set may be acquired triggered at the beginning of each heart cycle included in the acquisition of the second image data set, and with an acquisition rate such that the phases of the second image data set match phases in each of the heart cycles covered by the first image data set.

The heart rate, e.g. the length of a heart cycle, may does not change abruptly and remains essentially constant at least at the time scales used for imaging. While the following heart cycle and its duration is, of course, not known in advance, the heart cycle and its duration may be predicted with a very high probability as similar to the last few heart cycles. The predictability provides choosing the acquisition rate such that the phases of the first and second image data sets at least essentially match. The acquisition rate is chosen on the predicted heart cycles based on information on past heart cycles, for example, based on the assumption of the heart rate remaining at least essentially constant. Thus, "with an acquisition rate such that the phases of the acquired x-ray image data set match phases of the first x-ray image data set" is to be understood as describing the process or step of choosing the acquisition rate, not the result to be (in any case) achieved. An assumption used in this step is that the heart rate will remain at least essentially constant over the heart cycles included in the acquisition. Therefore, the length of the heart cycles is known, and the acquisition rate may be chosen such that the phases of the second image data set at least essentially match the phases of the first image data set, as long as the assumption holds true. The heart beat rate at the beginning of the acquisition of the second image data set may be measured.

Alternatively, the heart motion may be influenced such that the heart rate remains constant by using a cardiac pacemaker. However, due to the known stability of the heart rate, that remains essentially constant over a typical image acquisition, a pacemaker may not be needed. Exceptional cases, in which the heart rate does not remain constant during the triggered acquisition, will be discussed below. For example, the acquisition rate may be adapted, and/or the acquisition may be aborted and, for example, restarted as soon the heart rate remains (at least essentially) constant again.

The x-ray source of the x-ray device is thus not controlled continuously with the acquisition rate but synchronized with the beginning of each new heart cycle, such that x-ray images are, for each heart cycle covered by the acquisition, always recorded at the same positions in the heart cycle. The term "phase of the heart cycle" or "heart cycle phase" is used to refer to a specific moment during a heart cycle. For example, a heart cycle phase may thus describe a certain time interval during the heart cycle, during which no strong movements occur. If a heart cycle is denoted as running from 0% to 100%, phases may be denoted by percentage values.

An embodiment provides that a defined starting point during each heart cycle is used, such that when using a corresponding acquisition frequency, additional x-ray images taken during these heart cycles will always show corresponding phases, for example, also in acquisitions of x-ray image data sets over multiple heart cycles within the same x-ray image data set. There may be at least three images taken during each heart cycle, however, there may be two images during a heart phase, such that the term "rate" shall also cover this case. The electrocardiogram (ECG) triggering as defined above is not restricted to the second x-ray image data set but may also be used for the first x-ray image data set, while using the same trigger event in the heart cycle, that may be the R-wave. For example, in acquisitions of the first x-ray image data set spanning multiple heart cycles, x-ray images recorded in different heart cycles may also correspond in heart cycle phase.

Embodiments provide ECG-synchronous acquisition of x-ray data sets, increasing the accuracy and robustness in comparison to a non-ECG-synchronous acquisition technique.

The triggering may be performed at the R-wave of the heart cycle. In an embodiment the beginning of each heart cycle covered by the acquisition that triggers the acquisition of the second x-ray image data set is the R-wave of the heart cycle. The R-wave may be detected reliably by ECG measuring devices and has already been proposed as a trigger for certain imaging applications. Besides the R-wave also other significant features of the ECG may be used to define a beginning of the heart cycle, for example the Q-, S- or T-wave.

In an embodiment, at least one of the at least one first x-ray image data set is a contrast-enhanced anatomy data set and at least one of the at least one second image data set includes intra-operational fluoroscopy images. The fluoroscopy images are displayed overlaid or fused with anatomy images of the first x-ray image data set including the same heart cycle phase. The first x-ray image data set depicts the anatomy and is used as a background for current fluoroscopy images depicting an instrument used in a minimally invasive intervention. A contrast-enhanced anatomy data set may also be called a "dynamic road map". Embodiments provide for ECG-synchronous acquisition of the dynamic road map, that may be ECG-synchronously overlaid to the fluoroscopy images depicting the medical instrument used in the minimally-invasive intervention. The accuracy of overlaying/fusing the dynamic road map is considerably increased. Since the phases of the fluoroscopy images correspond to the phases of the contrast-enhanced anatomy data set by adequately controlling their acquisition anyway, it is sufficient to record the dynamic road map over one heart cycle with one contrast agent filling only as opposed to using multiple heart cycles for acquisition of a dynamic road map. Embodiments reduce patient x-ray dose and contrast agent. In other embodiments, image data sets are evaluated together, for example when comparing structures in these data sets or deriving other results.

The contrast-enhanced anatomy data set and the fluoroscopy images are acquired using the same x-ray device, for example, with the patient positioned for the operation to be performed. The first x-ray image data set and the second x-ray image data set are inherently registered to one another, facilitating the combined evaluation/overlay or fusion. The x-ray device may be an angiography device, for example, including a C-arm, to which the x-ray source and the x-ray detector are mounted at opposing ends.

In embodiments, the contrast-enhanced anatomy data set is also acquired triggered at the beginning of each heart cycle covered by the acquisition. If multiple heart cycles are covered, at the beginning of each heart cycle, synchronization occurs by re-starting the acquisition timing with the adequate acquisition rate. The first heart cycle or, if only one heart cycle is acquired, the only heart cycle is acquired ECG-triggered by starting the acquisition at the beginning of the heart cycle, e.g. the occurrence of the R-wave. Thus, the ECG-triggering is also used during the acquisition of the contrast-filled blood vessels over at least one heart cycle. The recorded x-ray images are stored as dynamic road map.

In an embodiment, the contrast-enhanced anatomy data set may include digital subtraction angiography images (DSA images). Mask images and fill images are matched in heart cycle phase by acquiring the images triggered at the beginning of each heart cycle covered using an acquisition rate such that the phases of the mask images and the fill images match. It is thus possible to acquire mask images during at least one heart cycle natively, that is, without using contrast agent, and acquire fill images during at least one further heart cycle after contrast agent has been administered. Due to both acquisitions performed ECG-synchronized, the phases match such that the mask images may be subtracted from the fill images to create a dynamic DSA road map. The dynamic DSA road map facilitates blood vessel segmentation significantly since the detection algorithms for contrasts-filled blood vessels are not distracted by other native structures in the images.

In an embodiment, the acquisition rate is chosen according to a current heart rate or adapted to a current heart rate. A possible parameterization for the acquisition rate may be to require a certain number, for example at least three, of x-ray images to be taken during each heart cycle, such that, depending on a current heart rate, the acquisition rate may be chosen such that the corresponding number of x-ray images equidistant in time may be acquired. The synchronization may also extend to the acquisition rate. If, in an example, 15 images are to be acquired during each heart cycle, the acquisition rate may be chosen appropriately. If the heart rate is 60 beats per minute and 15 images are to be acquired, each 67 milliseconds a new x-ray image is taken. With each beginning of a new heart cycle, e.g. R-wave, the timing may be restarted/synchronized to acquire x-ray images in the same heart cycle phases.

Independent of the definition of the acquisition rate, for example if an acquisition rate, e.g. 15 images per second, is predetermined, the heart rate and thus the duration of heart cycles may change during an acquisition procedure or between acquisition procedures, for example between acquisition of the first x-ray image data set and the second x-ray image data set. Embodiments may also react to changes in heart rate. ECG measuring devices also measure the heart rate anyway during an acquisition, for example by continuously averaging over a number of the last heart cycles. If the heart rate changes, the acquisition rate may be adapted to obtain matching phases of single images as accurately as possible. The adaptation may also take place dynamically during an acquisition process, for example during acquisition of the second image data set.

In an embodiment, the acquisition rate is chosen as a reference acquisition rate describing the phases to be acquired during a reference heart rate multiplied with the ratio of the current heart rate to the reference heart rate. The reference heart rate may be defined by the first heart cycle acquired and/or the reference acquisition rate may be chosen by a user, as further discussed below. The timing to be used, for example defined by the first heart cycle acquired, may also, for example, be redefined in percentage values between 0 and 100%. The duration 0 to 100% corresponds to the R-R interval. The timing may be adapted to natural fluctuations of the duration of the R-R interval/heart cycle. In the case of the creation of a dynamic road map and the subsequent application of this road map to fluoroscopy images, the acquisitions follow each other close in time such that the heart rate and thus the motion pattern of the heart do not have change severely.

The triggered acquisition may be started only if a stability criterion describing the heart rate remaining constant is fulfilled. To exclude time intervals of a regular heartbeat, verification that the heart rate is stable enough to acquire x-ray images using ECG triggering may be provided. A stability criterion is used providing that the heart rate does not fluctuate in average more than a predetermined threshold. The fulfillment of the stability criterion may also be displayed to a user starting the acquisition manually.

The acquisition rate may be chosen dependent on user input. The user input may be, for example choosing a certain number of images per heart cycle to be acquired. However, the user may also choose a certain acquisition rate that may be adapted later on during the acquisition as described above. It is also possible that the user input is constrained, for example, if certain requirements are to be met. If, for example, the first x-ray image data set is a four-dimensional CT data set with a predetermined number of phases for which a volume image is included, the user may be confined to using integer divisors of the number of phases contained in the four-dimensional CT data set. Corresponding constraints may also result when using a dynamic route map acquired before. Reducing the number of phases imaged for the second x-ray image data set may also be advantageous to further reduce patient x-ray dose.

In an embodiment, at least one of the at least one first x-ray image data set may be a four-dimensional CT data set including volume images for phases equidistant in time. The acquisition rate for the remaining x-ray data set is chosen such that all acquired phases match a phase of a volume image of the CT data set. Four-dimensional (3D+t) CT data sets may be used, that include a certain timing that may be transferred to the acquisition of further x-ray data, for example second x-ray image data sets. For example, the duration of the heart cycle may again be assumed as 100% such that the timing described by the phases of the volume images of the four-dimensional CT data set may be converted into the corresponding timing during acquisition of further x-ray data, for example fluoroscopy images, e.g. also adapting the acquisition rate to the current heart rate.

In the application of dynamic road mapping, the four-dimensional CT data set may be considered pre-operational 3D+t data, that may also be used as showing the anatomy in a road mapping procedure, assuming that heart motion is similar, even if the heart rates differ. First image data sets from other modalities, that may be registered to the x-ray device/x-ray data, may be used as four-dimensional pre-operational data sets, for example magnetic resonance (MR) data.

The region of interest may not only subject to heart motion, but also may be subject to breathing motion. While certain first and/or second x-ray image data sets may also be acquired during breath holds, in an embodiment a breathing motion correction may be added. The x-ray data set is corrected for breathing motion, for example, by a pixel shift algorithm. Suitable algorithms for breathing motion correction, e.g. pixel shift algorithms, are known.

In an embodiment, an x-ray device includes a control device configured to perform a method as described above. All remarks relating to the method are also applicable to the x-ray device. The x-ray device may be an angiography device, for example including a C-arm with an x-ray source and an x-ray detector at opposing ends thereof.

An x-ray device may include an acquisition arrangement including an x-ray source and an x-ray detector and/or an ECG measuring device for generating a trigger signal at the beginning of each heart cycle to be sent to the control device. The trigger signal may be used to control the x-ray source to provide ECG-synchronized acquisition of x-ray images. In an embodiment, the control device may include a control unit configured for controlling the acquisition of x-ray data synchronized with the trigger signal using an acquisition rate, and an image evaluation unit configured for assigning a heart cycle phase to acquired x-ray images and evaluating the first x-ray image data set and the second x-ray image data set together. The control device may further include an adaptation unit for adapting the acquisition rate to a current heart rate and/or a user interface for interacting with a user and/or other units relating to other embodiments of the method.

A computer program may be directly loaded into a storage device of a control device of an x-ray device and may include a computer program configured to perform the method described herein when the computer program is executed in the control device of the x-ray device. The computer program may be stored on an electronically readable storage medium that includes electronically readable control information stored thereon, that may include a computer program. The control information is configured to perform a method described herein when using the storage medium in a control device of an x-ray device. The storage medium may be a non-transitory storage medium, for example a CD-ROM.

BRIEF DESCRIPTION OF THE FIGURES

FIG. 3 depicts an example for the applied timing according to an embodiment.

DETAILED DESCRIPTION

Figure 1:
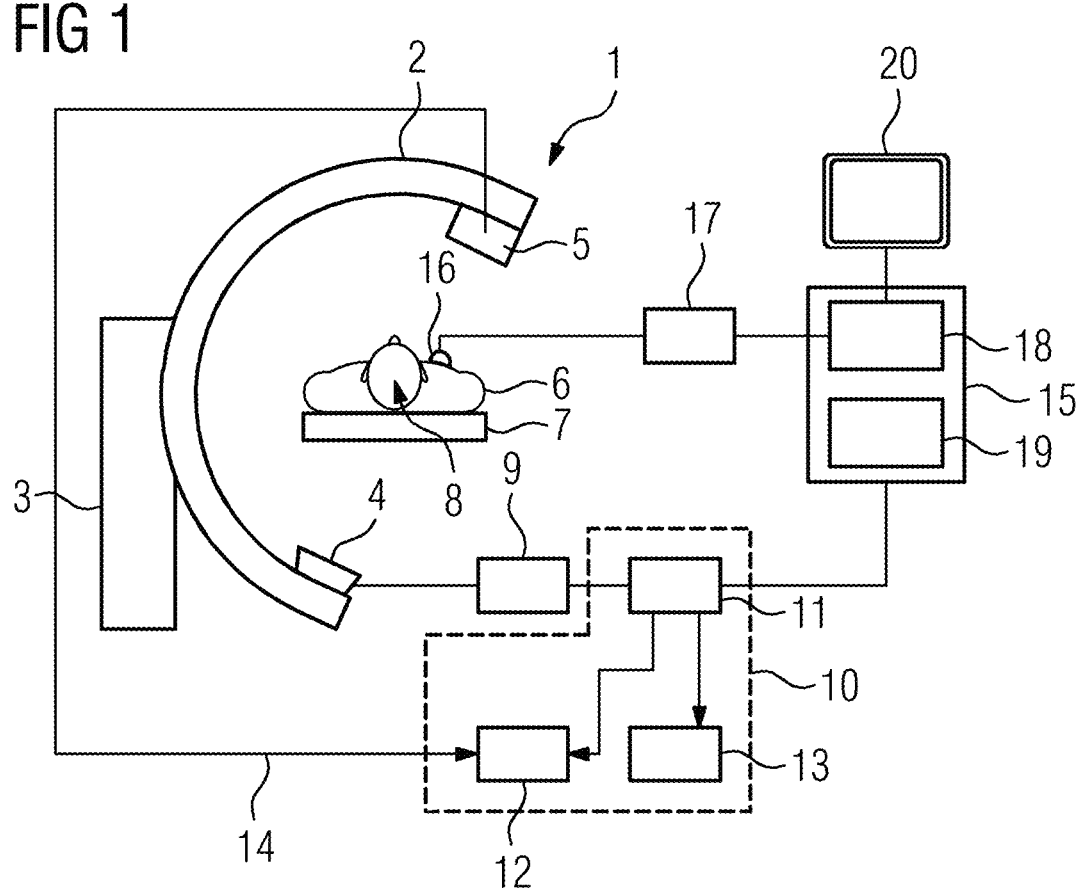
FIG. 1 depicts an x-ray device according to an embodiment.

FIG. 1 depicts an example x-ray device 1, that is an angiography device including a C-arm 2 supported by a support 3. To opposite ends of the C-arm 2, an x-ray source 4 and an x-ray detector 5 are mounted. The C-arm may be positioned relatively to a patient 6 supported by a patient table 7 to realize different acquisition geometries.

The x-ray device 1 may, for example, be used to survey a minimally invasive intervention/operation of a patient 6, for example, for tracking a medical instrument 8 inserted into a patient 6, for example a catheter.

A voltage for the x-ray source 4, e.g. an x-ray tube, is provided by an x-ray generator 9 that receives control signals from control device 10, that is configured to perform the steps of a method. The control device 10 includes at least a control unit 11, an image evaluation unit 12 and a user interface 13. The image evaluation unit 12 also receives raw x-ray data from the x-ray detector 5 according to arrow 14.

The x-ray device 1 further includes an ECG measuring device 15 including electrodes 16 to be placed on the patient 6, a signal amplifier 17, an evaluation unit 18 and a trigger signal generating unit 19. The ECG measuring device 15 may also include a display 20. The Display 20 may, for example, indicate fulfillment of a stability criterion describing the heart rate remaining constant in a certain interval. If the stability criterion is fulfilled, an ECG-synchronized acquisition of x-ray data may be performed as further described below.

Figure 2:
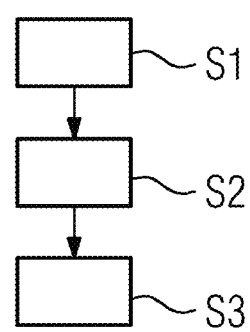
FIG. 2 depicts a flow chart of a method according to an embodiment.

An example of a method according to an embodiment is described with respect to FIG. 2. In this example, a dynamic road mapping procedure during a medical intervention is to be performed.

At act S1, a user may input data regarding the acquisition rate using user interface 13, by selecting a number of x-ray images to be acquired during a heart cycle. Different values may be chosen for acquiring a first x-ray image data set, e.g. a contrast-enhanced anatomy data set (dynamic road map), and a second x-ray image data set, e.g. fluoroscopy images showing the instrument 8. However, the second value may be a divisor of the first value to facilitate matching heart cycle phases, as further described below. If pre-operative image data, for example a four-dimensional CT data set, is used, that already provides a given number of volume images at certain phases during the heart cycle, the number of x-ray images may be constrained that may be acquired during each heart cycle regarding fluoroscopy images to be overlaid onto the three-dimensional volume images of the pre-operative image data.

At act S2, the contrast-enhanced anatomy data set is acquired using the x-ray device 1. In an embodiment, a contrast agent is administered, and a certain number of x-ray images are recorded during a single heart cycle. If the stability criterion is fulfilled, the ECG measuring device 15 transmits an ECG trigger signal at the beginning of a heart cycle, for example, when detecting the R-wave, to the control device 10, e.g. the control unit 11, that instantly generates a series of control signals to the x-ray generator 9 implementing an acquisition rate, e.g. calculated from the duration of a heart cycle in the current heart rate and the user input named above. If the heart rate is 60 beats per minute and the number of images to be acquired during a heart cycle is 15, the corresponding acquisition rate is 15 images per second, e.g. one image every 67 milliseconds.

The result of this acquisition is stored as a dynamic road map in a storage device of the control device 10, for example, the image evaluation unit 12.

X-ray images of the contrast-enhanced anatomy data set may also be acquired over multiple heart cycles. Each time a trigger signal is received from the ECG measuring device 15, a control unit 11 re-starts the acquisition process, thus synchronizing with the heart cycle to image the same phases of the heart cycle in each of the heart cycles covered by the acquisition.

FIG. 3 depicts a simplified example of three acquisitions per heart cycle. As depicted, the beginning of each heart cycle 21 and thus the duration of a heart cycle 21 is defined by respective R-waves 22 in the ECG signal 23 measured by the ECG measuring device 15. As soon as an R-wave 22 is detected, a corresponding trigger signal 24 is transmitted to the control device 10, as discussed above. In response to the trigger signal 24, that acts as a synchronization signal, an acquisition timing is started in control unit 11, beginning to record x-ray images of the region of interest in the patient, that is subject to heart motion, with a corresponding acquisition rate, for example, assuming a heartbeat rate average of 60 beats per minute, of three images per second and, in other words, one image every 333 seconds. The corresponding control signals 25 from the control unit 11 to the x-ray generator 9 are shown in the bottom line of FIG. 3.

As depicted, independently of the duration of a particular heart cycle 21, the imaging always starts anew on reception of a trigger signal 24, assuring acquisition of x-ray images in phases of the heart cycle as similar as possible.

In an embodiment, the contrast-enhanced anatomy data set may be acquired as a DSA data set. During a first heart cycle mask images are acquired without contrast agent in the region of interest of the patient. Subsequently, after a contrast agent has been administered, during a second heart cycle, fill images are acquired using the same timing as during the acquisition of the mask images in a further heart cycle. If the heart rate has changed between these acquisitions, the acquisition rate may be configured to the new heart rate, using the heart rate during acquisition of the mask images as a reference heart rate and the acquisition rate during the acquisition of the mask images as reference acquisition rate. The timing is re-used in an adapted form to obtain mask images and fill images similar in heart cycle phase, such that the mask images may be subtracted from the fill images corresponding in heart cycle phase to obtain DSA images.

During the intervention, at act S3, the timing used to obtain the contrast-enhanced anatomy data set is again used to obtain fluoroscopy images of the patient 6 showing the instrument 8. Again, at the beginning of each heart cycle covered by the acquisition, when a trigger signal 24 is received, the acquisition of fluoroscopy images is started anew, thus synchronized with the heart cycles, using the acquisition rate, again adapted to the current heart rate. Thus, for each heart cycle phase of a fluoroscopy image, a corresponding dynamic road map image exists in the contrast-enhanced anatomy data set such that these images corresponding in phase may be fused and/or overlaid in the evaluation unit 12. The image evaluation unit 12 also assigns respective phases to acquired x-ray images according to the control signal 25/trigger signals 24.

The fused/overlaid images may be displayed using the display 20 and/or user interface 13 to provide a navigation/tracking 8 for the user, for example, the practitioner performing the minimally invasive intervention. It has been shown that this method of ECG-synchronizing leads to a significant stabilization of the fusion and/or overlay during dynamic road mapping procedures.

The x-ray data sets acquired, and the embodiments may be subject to an additional breathing motion correction, for example, using a pixel shift algorithm.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquiring x-ray data with at least one x-ray device, the method comprising:
   acquiring at least one first x-ray image data set over multiple heart cycles of a region of interest of a patient that is subject to heart motion, wherein the acquisition restarts at a beginning of each heart cycle of the multiple heart cycles independently of a duration of a particular heart cycle;
   acquiring, subsequent to acquiring the at least one first x-ray image data set, at least one second x-ray image data set of the region of interest, wherein the acquisition of the at least one second x-ray image data set is triggered at a beginning of each heart cycle of the multiple heart cycles and with an acquisition rate such that phases of the at least one second x-ray image data set match phases of the at least one first x-ray image data set; and
   fusing the at least one first x-ray image data set and the at least one second x-ray image data set together, wherein for each heart cycle phase of the first x-ray image data set a corresponding image exists in the second x-ray image data set; and
   displaying the fused image data sets;
   wherein the at least one first x-ray image data set is a contrast-enhanced anatomy data set and the at least one second image data set comprises intra-operational fluoroscopy images, wherein the intra-operational fluoroscopy images are displayed fused with the contrast-enhanced anatomy data set of the at least one first x-ray image data set including a same heart cycle phase.

2. The method of claim 1, wherein the acquisition of the at least one second x-ray image data set is triggered at a R-wave of the heart cycle.

3. The method of claim 1, wherein the contrast-enhanced anatomy data set and the fluoroscopy images are acquired using a same x-ray device.

4. The method of claim 1, wherein the contrast-enhanced anatomy data set comprises digital subtraction angiography images, wherein mask images and fill images are matched in heart cycle phase by acquiring them triggered at the beginning of each heart cycle covered using an acquisition rate such that the phases of the mask images and the fill images match.

5. The method of claim 1, further comprising:
   selecting the acquisition rate according to a current heart rate or adapted to a current heart rate.

6. The method of claim 5, wherein the acquisition rate is further selected as a reference acquisition rate describing the phases to be acquired during a reference heart rate multiplied with the ratio of the current heart rate to the reference heart rate.

7. The method of claim 1, wherein the triggered acquisition is started only if a stability criterion describing the heart rate remaining constant is fulfilled.

8. The method of claim 1, wherein the acquisition rate is dependent on user input.

9. The method of claim 1, wherein at least one of the at least one first x-ray image data set is a four-dimensional CT data set comprising volume images for phases equidistant in time, wherein the acquisition rate for a remaining x-ray data set is selected such that all acquired phases match phases of a volume image of the CT data set.

10. The method of claim 1, further comprising:
    correcting the x-ray data set for breathing motion using a pixel shift algorithm.

11. An x-ray device comprising:
    an x-ray source;
    an x-ray detector configured to acquire at least one first x-ray image data set over multiple heart cycles of a region of interest of a patient that is subject to heart motion, wherein the acquisition restarts at a beginning of each heart cycle of the multiple heart cycles independently of a duration of a particular heart cycle and at least one second x-ray image data set, subsequent to acquiring the at least one first x-ray image data set, of the region of interest, wherein the acquisition of the at least one second x-ray image data set is triggered at a beginning of each heart cycle of the multiple heart cycles and with an acquisition rate such that phases of the at least one second x-ray image data set match phases of the at least one first x-ray image data set; and a control device configured to evaluate the at least one first x-ray image data set and the at least one second x-ray image data set together;

wherein the at least one first x-ray image data set comprises contrast-enhanced anatomy images and the at least one second image data set comprises intra-operational fluoroscopy images, wherein the intra-operational fluoroscopy images are displayed fused with the contrast-enhanced anatomy images of the at least one first x-ray image data set including a same heart cycle phase.

12. The x-ray device of claim 11, further comprising:
a user interface configured to receive an input relating to a number of x-ray images to be acquired during the heart cycle.

13. The x-ray device of claim 11, further comprising:
an ECG measuring device configured to transmit an ECG trigger signal at the beginning of the heart cycle to the control device.

14. The x-ray device of claim 11, wherein the acquisition of the at least one second x-ray image data set is triggered at a R-wave of the heart cycle.

15. The x-ray device of claim 11, wherein the contrast-enhanced anatomy data set and the fluoroscopy images are acquired using a same x-ray detector.

16. An x-ray imaging system, configured to evaluate x-ray image data, the x-ray imaging system comprising:
a control unit including a computing device with a memory and at least one processor, the memory containing instructions by the at least one processor, wherein the computing device is configured to:

acquire at least one first x-ray image data set over multiple heart cycles of a region of interest of a patient that is subject to heart motion, wherein the acquisition restarts at a beginning of each heart cycle of the multiple heart cycles independently of a duration of a particular heart cycle;

acquire, subsequent to acquiring the at least one first x-ray image data set, at least one second x-ray image data set of the region of interest, wherein the acquisition of the at least one second x-ray image data set is triggered at a beginning of each heart cycle of the multiple heart cycles and with an acquisition rate such that phases of the at least one second x-ray image data set match phases of the at least one first x-ray image data set; and fuse the at least one first x-ray image data set and the at least one second x-ray image data set together, wherein for each heart cycle phase of the first x-ray image data set a corresponding image exists in the second x-ray image data set; and display the fused image data sets;

wherein the at least one first x-ray image data set comprises contrast-enhanced anatomy images and the at least one second image data set comprises intra-operational fluoroscopy images, wherein the intra-operational fluoroscopy images are displayed fused with the contrast-enhanced anatomy images of the at least one first x-ray image data set including a same heart cycle phase.

17. The system of claim 16, wherein the acquisition of the at least one second x-ray image data set is triggered at a R-wave of the heart cycle.

* * * * *